Figure 1:
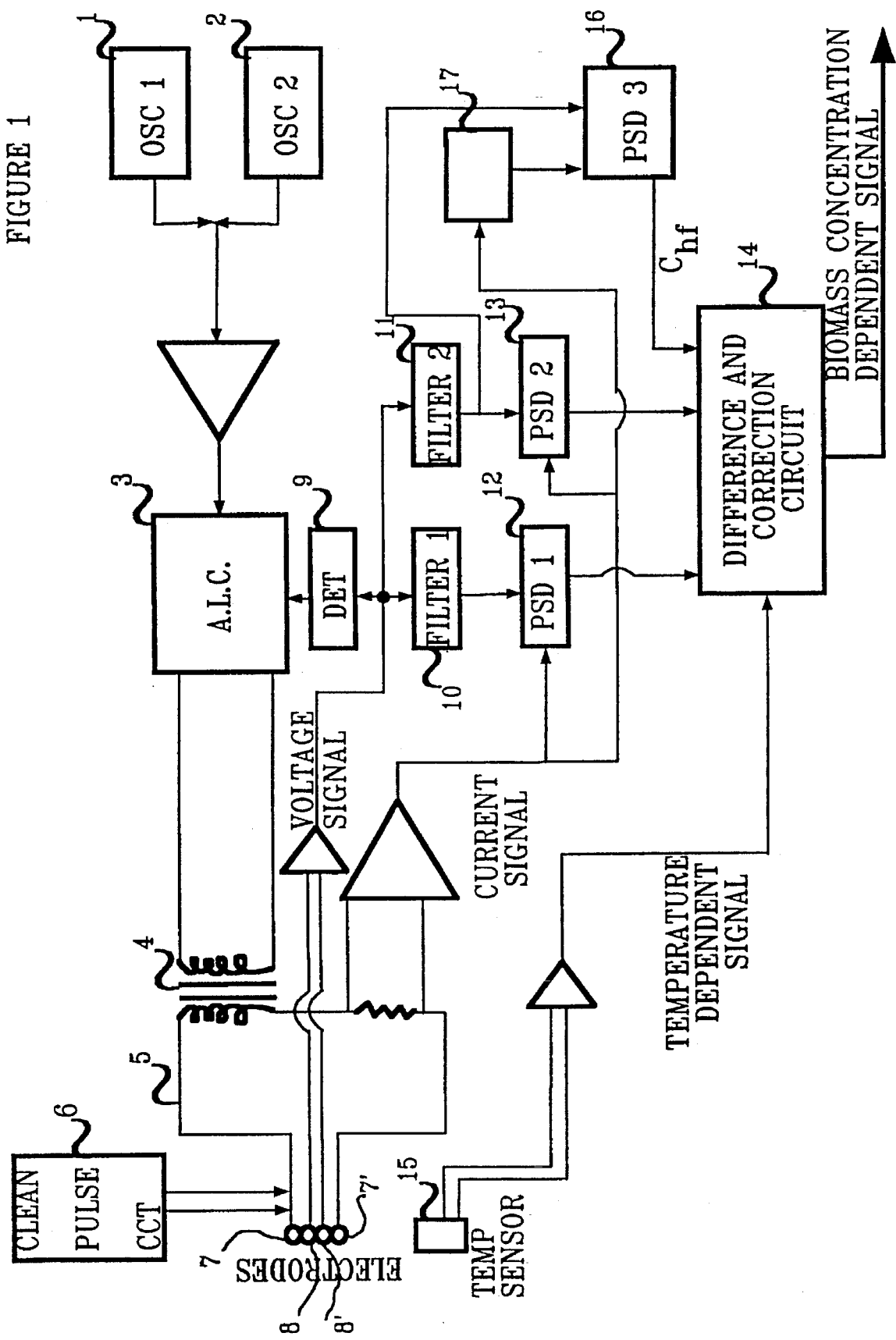

United States Patent [19]
Todd

[11] Patent Number: 5,551,281
[45] Date of Patent: Sep. 3, 1996

[54] METHOD FOR DETERMINING GAS HOLD-UP

[76] Inventor: Robert W. Todd, Bryncaemeilir, Machynlleth, Powys SY20 8QG, Great Britain

[21] Appl. No.: 244,359

[22] PCT Filed: Jun. 1, 1993

[86] PCT No.: PCT/GB93/00011

§ 371 Date: May 26, 1994

§ 102(e) Date: May 26, 1994

[87] PCT Pub. No.: WO93/14402

PCT Pub. Date: Jul. 22, 1993

[30] Foreign Application Priority Data

Jan. 7, 1992 [GB] United Kingdom .................. 9200246

[51] Int. Cl.$^6$ .......................... C12M 01/34; G01R 11/52; G01N 11/00
[52] U.S. Cl. .................. 73/19.01; 73/61.44; 73/54.15
[58] Field of Search .................. 73/19.01, 61.44, 73/54.15

[56] References Cited

U.S. PATENT DOCUMENTS

| | | | |
|---|---|---|---|
| 4,810,650 | 3/1989 | Kell et al. ........................ | 435/291 |
| 4,810,963 | 3/1989 | Blake-Coleman et al. ......... | 324/204 |
| 4,965,206 | 10/1990 | Kell ................................ | 435/291 |
| 5,260,667 | 11/1993 | Garcia-Golding et al. ......... | 324/694 |
| 5,272,444 | 12/1993 | Cox ................................ | 324/698 |
| 5,289,716 | 3/1994 | Schumacher ..................... | 73/54.19 |

*Primary Examiner*—Hezron E. Williams
*Assistant Examiner*—J. David Wiggins
*Attorney, Agent, or Firm*—Iandiorio & Teska

[57] ABSTRACT

A method and apparatus for determining gas hold-up in a fermentation culture, in which, prior to aeration and during fermentation, a high frequency alternating signal is input to electrodes in electrical contact with the culture, the magnitude of the reactive current signal leading the voltage in the electrode circuit is determined and the difference in said magnitudes prior to aeration and during fermentation is used as a measure of the gas hold-up. The system may be combined with various methods of measuring biomass to give a gas hold-up corrected value of biomass.

38 Claims, 4 Drawing Sheets

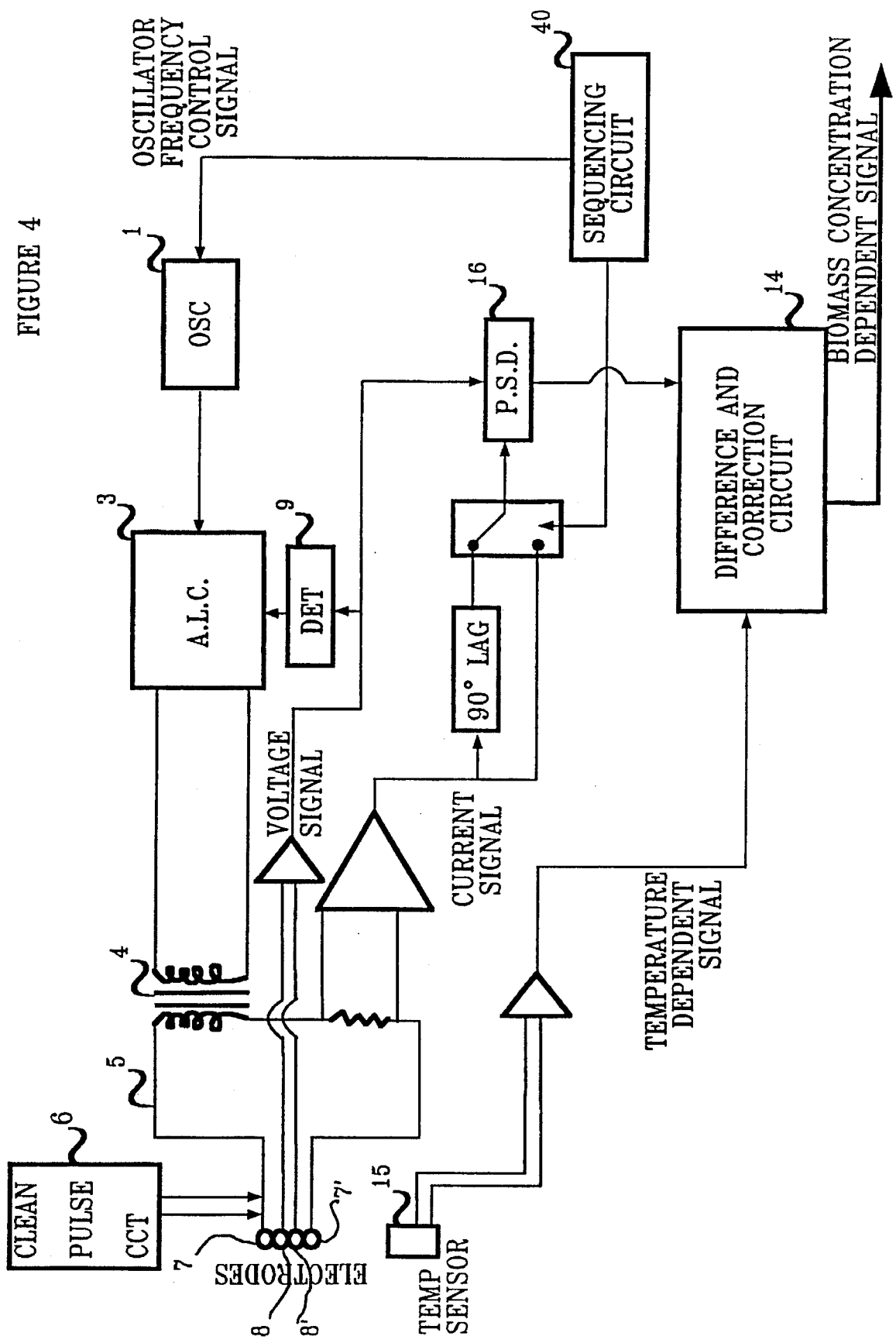

METHOD FOR DETERMINING GAS HOLD-UP

This invention relates to determination of gas hold-up in a fermentation process and has wider implications for determination of cellular biomass or biovolume and to processes in which such determination is made.

One of the most important variables in a fermentation or other process using biological cells is the reactor biomass concentration, that is the concentration of microbial or other biological cells in the reactor, because the productivity of a process under a given set of conditions is proportional to the biomass concentration.

For monitoring purposes during a fermentation it is particularly useful to be able to estimate the biomass on a real time basis rather than at some time in the past. This generally requires the utilisation of physical properties that can be measured in situ rather than properties which require sampling and analysis. However, the conditions within fermentation reactors do not lend themselves to the use of all physical techniques.

In prior artwork done by the Applicant European Patent No. 0281602 and published European Patent Application No. 0282532 describe a method and apparatus for the determination of biomass in a culture medium in which a signal dependent on the electrical capacitance or dielectric permittivity is generated, at a suitable frequency or range of frequencies, between electrodes mutually spaced in the medium, and determining from the capacitance or permittivity dependent signal, the volume of total liquid in a net volume fraction enclosed by the cytoplasmic membranes of the cells.

The basis of this approach is that biological cells, in contrast to macromolecules, ionic solutions and gas bubbles, have molecularly thin lipid membranes which (when measured at suitable frequencies) can be shown to have a large electric capacitance per unit membrane area. When suspended in a conductive medium, the measured capacitance exhibits a frequency dependence known as the beta dispersion. By measuring the capacitance at suitable frequencies it is possible to estimate the magnitude of the beta dispersion and in turn the biomass concentration.

In a development of the above approach a conductance signal representative of the culture conductivity at respective high and low frequencies may also be used.

These methods work in many processes, but a problem that limits their accuracy is the varying quantity of gas that may be present in the culture. During fermentation the medium in a bioreactor may consist of multiple phases o gases, liquids and solids, and because the permittivity of gases is significantly lower than that of liquids, the presence of gas bubbles decreases the measured capacitance or conductance of the suspension causing errors in the biomass concentration estimate. This problem can be minimized by maintaining a constant level of aeration during the reaction and calibrating the apparatus for that level. However in some circumstances it may not be convenient or possible to keep gas hold-up constant even when aeration rate is constant and it is desirable to have a measuring technique for gas hold-up.

Accordingly the invention provides a method of determining gas hold-up in a fermentation culture, the method comprising, prior to aeration and during fermentation, inputting a high frequency alternating signal to electrodes in electrical contact with the culture, determining the magnitude of the current signal leading the voltage in the electrode circuit and using the difference in said magnitudes prior to aeration and during fermentation as a measure of the gas hold-up.

The invention also provides apparatus for determining gas hold-up in a fermentation culture, the apparatus comprising means for inputting a high frequency alternating signal to an electrode circuit that includes electrodes in electrical contact with the culture, means for inputting the voltage over the inter electrode gap to a phase sensitive detector, means for imposing a 90° phase lag on a current signal from the electrode circuit and for inputting said lagged signal to the phase sensitive detector to produce a signal related to a quadrature component of current in the electrode circuit.

Figure 2:
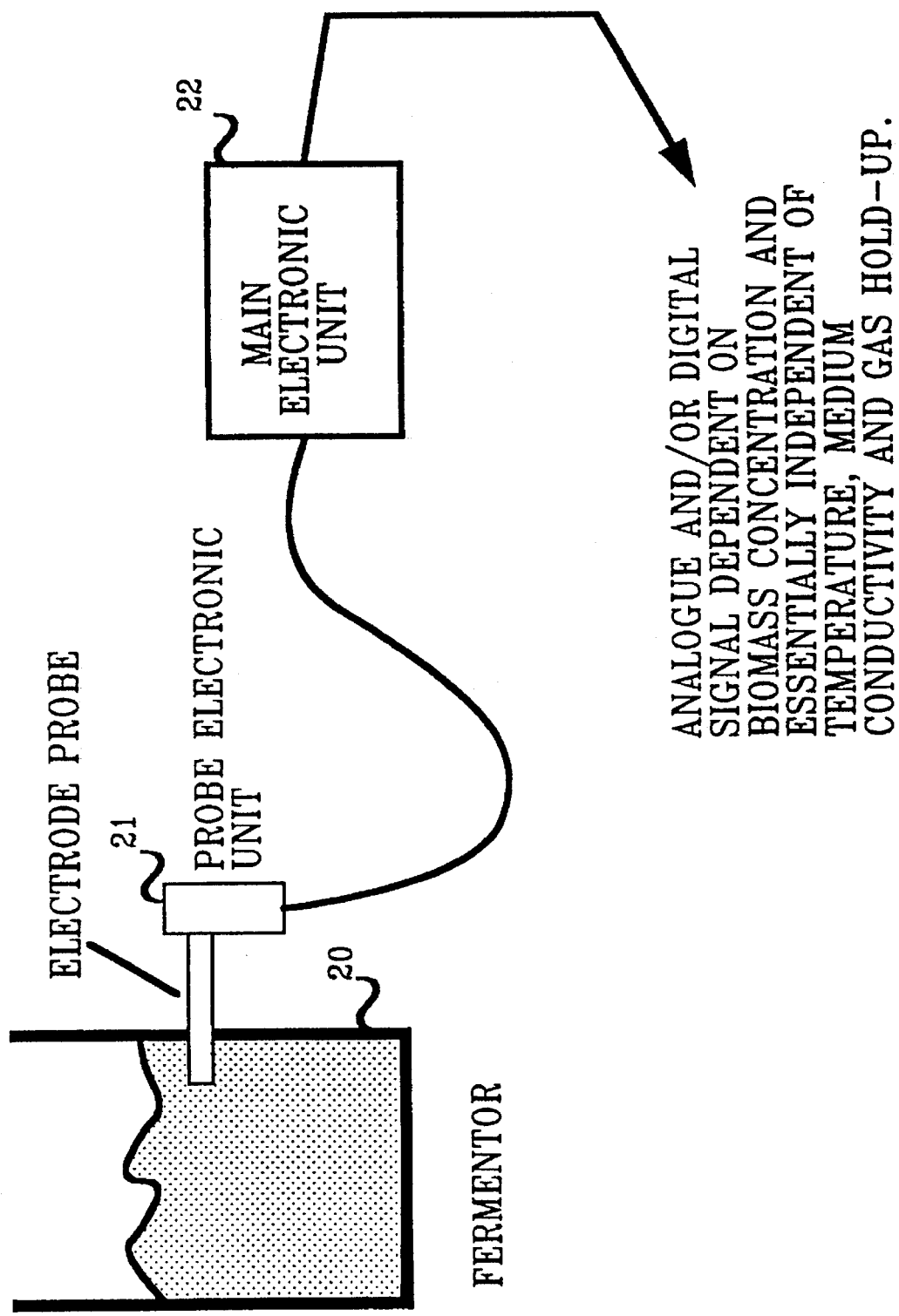

The invention is now described by way of example with reference to the accompanying drawings in which:

FIG. 1 illustrates a circuit for combined conductance measurement of biomass and gas hold-up correction;

FIG. 2 schematically illustrates a fermentation reactor provided with the equipment of FIG. 1.

Figure 3:
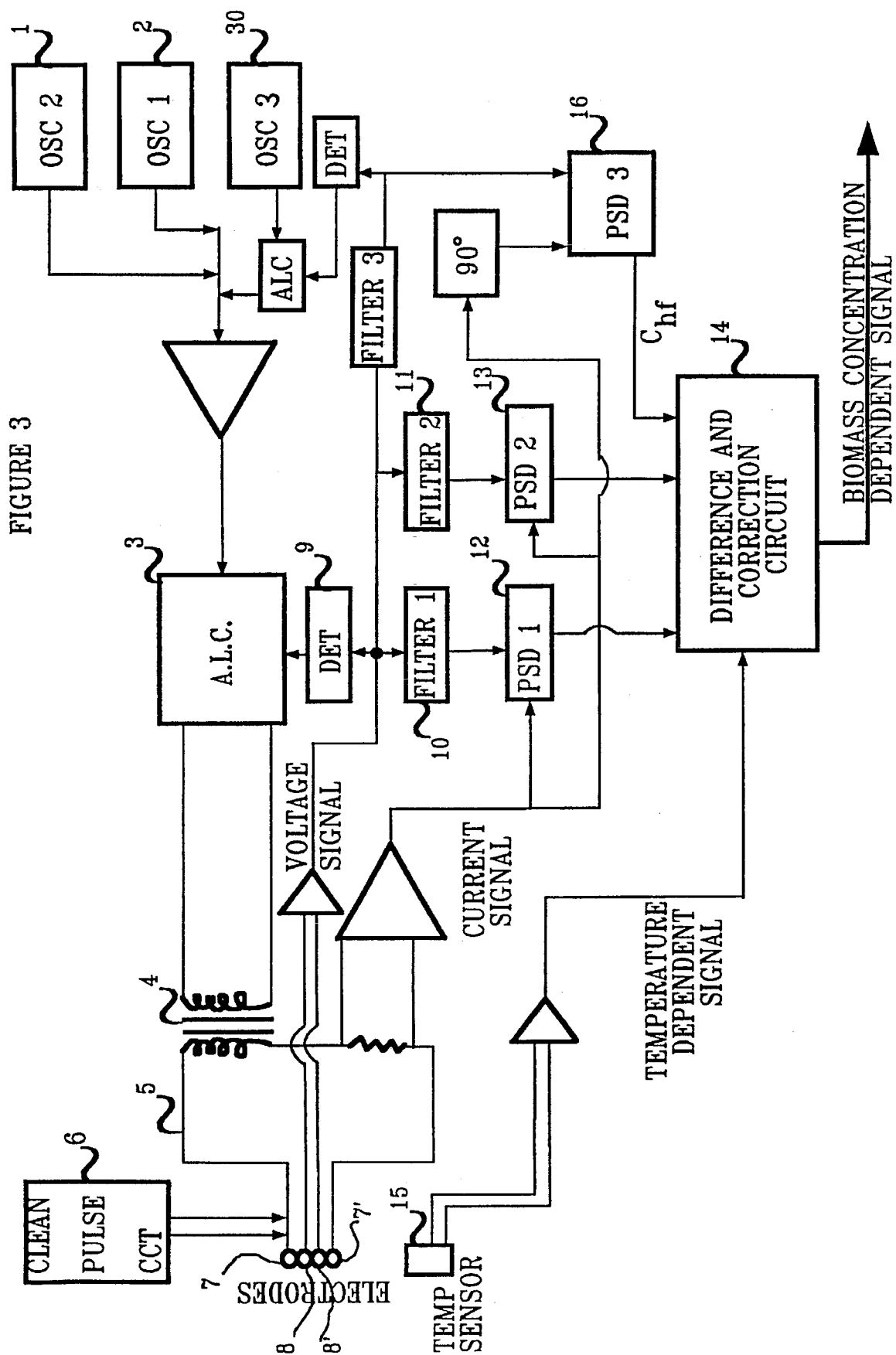

FIG. 3 schematically illustrates an alternative circuit using a separate frequency for gas hold-up measurement; and FIG. 4 schematically illustrates a circuit in which frequency signals are applied sequentially rather than simultaneously.

As mentioned above, the electrical behaviour of a cellular suspension or tissue is strongly dependent on frequency, the frequency dependent change in characteristic relative to the value for an aqueous solution being termed a 'dispersion'. Three major sources of dispersion are recognised and are termed alpha, beta and gamma dispersion. Beta dispersion, as explained in our prior European Patent No. 0281602, is a property of intact cells and is therefore of use in analysing cell content via the electrical behaviour of media incorporating intact biological cells. Alpha and gamma dispersions are not predictably dependent upon intact cell concentration, and occur, respectively, at lower and higher frequencies than beta dispersion being related to mobile ions at cell surfaces and dipolar rotation.

Beta dispersion is essentially due to intact cells having a poorly conducting, relatively ion-impermeable, cellular membrane, whereas the interior of the cell is relatively conducting. The position of the beta dispersion curve on the frequency axis is a function of cell radius, membrane capacitance and internal and external electrical conductivities, whilst the magnitude of the dispersion depends upon the concentration, in terms of percentage volume, of the cells in the medium as well as other variables such as cell size.

Our previous patent utilises a calibrated measurement of capacitance in the frequency range of the beta dispersion as a measure of biovolume. However as measurement of capacitance in higher conductance media becomes more difficult, an alternative technique utilising conductance measurements has been developed. This alternative technique utilises the fact that at lower frequencies cell membranes block the flow of current through the interior of the cell, but at higher frequencies current flows through the cell via the membrane capacitance. It can be shown that the difference in conductivity through the suspension at different frequencies equals ¾ (volume fraction×internal cell conductivity), i.e. it depends upon, inter alia, the radius and volume fraction occupied by the cells.

During fermentation the liquid media in reactors are aerated and although the rate of aeration can be maintained constant so as to maintain, as far as possible, constant gas hold-up, there are occasions when changes in the rate of aeration are desired. Also, as fermentation progresses changes in viscosity may also result, giving rise to changes in gas hold-up.

The presence of gas bubbles, reducing the unit volume concentration of water, reduces the capacitance over the whole range of frequencies used in biomass measurement because of the lower permittivity of gas compared with water. The change in capacitance caused by gas hold-up has an effect both on background capacitance and also upon the measured magnitude of the $\beta$ dispersion itself because the gas bubbles also displace cells. Hence in the capacitance measurement technique the measured $\beta$ dispersion changes with gas hold-up.

In the above described conductance method water displacement also changes the measured values. In this technique the difference between two measurements is taken, so the background element of the change maybe eliminated, but this still leaves the inaccurancy in measured dispersion arising from displacement of the cells.

The present invention is principally concerned with enabling measurement of gas hold-up in order to establish corrected values for biomass (derived from biovolume) as measured for example by either of the techniques referred to above.

At high frequencies, ideally above the $\beta$ dispersion range, capacitance is principally determined by water content. Thus in the invention it is proposed to utilise a high frequency capacitance measurement before onset of aeration, and during reaction. Subsequent changes in the capacitance at the higher frequency after onset of aeration and reaction are then attributed directly to gas hold-up, for example a 20% reduction in capacitance indicating approximately 20% gas content.

This estimate of gas hold-up can be used to correct the biomass concentration estimate provided by means such as the capacitance method in EP 0281602 or, as described hereinafter, the conductance method. In either instance the following relationship applies:

$$\text{Corrected biomass concentration estimate} = \frac{100}{100 - G.F.(\%)} \times \text{direct biomass concentration signal}$$

$G.F.$ = Gas Fraction %

Conventional sampling followed by laboratory analysis methods, i.e. after the gas bubbles have cleared from the sample, measure corrected biomass and thus the present invention enables in-situ determination of the conventional analysis amounts, which may be subsequently verified from time to time.

Preferably the frequency used for the capacitance measurement is above the $\beta$ dispersion range. In some instances measurements may need to be taken within the top end of the $\beta$ dispersion range, for example if the dispersion range is very extended. This would cause some inaccuracy of the gas fraction estimate; if this is unacceptably large, a curve fitting technique may be used to determine the true high-frequency (i.e. above $\beta$ dispersion) capacitance value.

A measure of gas fraction, as opposed to just aeration rate, is also useful in its own right as a means of monitoring and assisting in the optimisation of some fermentations.

A circuit for a preferred embodiment of the invention is shown in FIG. 1, in which a gas hold-up measurement is combined with conductance measurement to determine biomass. The conductance measurement utilises measurement at two frequencies generated by oscillators 1 and 2, with oscillator 2 at high frequency. The outputs of the oscillators are combined, amplified, input to an automatic level control 3 and then to the primary winding of an isolating transformer 4. Induced oscillations occur in an electrode circuit 5 connected to the transformer secondary winding.

To alleviate electrode polarisation effects there are two sets of electrodes, outer current electrodes 7, 7' through which the current passes to and from the culture and at which any polarisation effects will occur, and an inner set of voltage electrodes 8, 8' which sample the voltage over a gap intermediate the current electrodes, immune from polarisation. A separate circuit 6 for applying pulses to the electrodes for cleaning purposes from time to time may also be provided. Other electrode configurations may also be used.

The voltages sensed by the electrodes 8, 8' are amplified and input to a detector 9 and to band-pass filters 10 and 11. Detector 9 completes a feedback loop for automatically controlling the gain of the applied voltage by means of the automatic level control 3. It will be appreciated that the voltage over the electrodes 8, 8' is a combination of voltages having the two different oscillator frequencies and the band-pass filters 10 and 11 are tuned, respectively, to pass the lower and higher frequency voltage signals which constitute phase reference signals for the phase detectors 12 and 13.

From the band-pass filters the voltage signals are input to respective phase sensitive detectors 12 and 13 which also receive a current signal input from the electrode circuit, which for example may be taken over a suitable load. The output from the phase sensitive detectors 12 and 13 are signals corresponding to the magnitude of the component of the current signal that is in phase with the respective reference voltage signal, i.e. proportional to the conductance. Thus conductance value signals for the lower and higher frequencies are output, respectively, from phase sensitive detectors 12, 13 into a comparator within a difference and correction circuit 14.

The circuit 14 also receives a temperature dependent signal from a temperature sensor 15 located close to the electrodes in the medium which provides a temperature compensation adjustment from a precalibrated reference.

The gas hold-up correction is also input to circuit 14. This utilises the higher frequency voltage signal, taken after band-pass filter 11 and input to a third phase sensitive detector 16, along with the current signal. In order to establish the extent of gas hold-up a measure of the capacitance at the higher frequency is required, and thus prior to the phase sensitive device the current signal is input to a phase shifter 17, which imposes a $\pi/2$ lag, so that the output of phase sensitive detector 16 is indicative of the magnitude of the current signal leading by $\pi/2$ with respect to the voltage in the electrode circuit, i.e. representative of the capacitance value. This capacitance value is used by the correction circuit, using pre-calibrated values, to apply a gas hold-up correction to the final biomass concentration dependent signal output from circuit 14.

It will be realised that if the different frequency signals are applied in rapid succession, rather than simultaneously, signal processing of the different frequencies may be handled within a single processor; for example the signals may all go in sequence to a single phase sensitive device. This approach reduces the requirement for this frequency-selective filtering and may be preferred for this reason. A suitable circuit is shown in FIG. 4, using only a single oscillator 1, a sequencing circuit 40 and with a sample-hold facility in the difference and correction circuits 14.

FIG. 2 schematically illustrates a fermentation reactor 20 provided with conductance biovolume measuring equipment as previously described. In order to reduce equipment introduced errors the electrode voltage and current sensing circuits including an amplification stage are preferably incorporated in a probe module 21 close to the electrode circuit. The main electronic processing unit 22 may then be located remote from the apparatus.

For simplicity the apparatus and method for combined biomass measurement and gas hold-up correction have been described in terms of utilising a high and low frequency. More than one high and low frequency may be utilised and the results used to compute biomass concentration and other parameters or used for other correction purposes. In some cases, the gas hold-up capacitance is preferably measured at a third, higher frequency, than the conductance measurement frequencies with suitable additional circuitry as shown in FIG. 3 with oscillator 30. Alternatively, the high frequency capacitance measurement may be incorporated into a capacitance measuring biomass arrangement to correct the biomass concentration signal for changes in gas hold up. In some instances measurements may need to be taken within the top end of the β dispersion range rather than clear of it, for example if the dispersion range is very extended. In such instances, as with the conductance method above, it is possible to utilise either separate or common high frequency signals for the biomass concentration and gas hold-up measurement.

Also, different electrodes may be used for the gas hold-up measurement and biomass measurements.

The block diagrams shown herein have been simplified for illustrative purposes. Production versions of the systems shown would require further feedback systems for automatic trimming of zero level drift and phase response of the electronics and cables.

I claim:

1. A method of determining gas hold-up in a fermentation culture having a concentration of biological cells in a biomass, the method comprising the steps of first prior to aeration and then during fermentation of the culture inputting inputting to the culture electrically coupling an alternating signal of a frequency which is above the range of frequencies at which β dispersion occurs, determining the magnitude of reactive current signal leading voltage in the culture and using measured difference in said magnitudes determined prior to aeration and determined during fermentation as a measure of the gas hold-up.

2. The method of claim 1 further comprising determining biovolume in a culture and utilizing said gas hold-up determination to provide a corrected biovolume estimate.

3. The method of claim 2 in which the biovolume is determined by inputting respective high and low frequency alternating signals to the culture, deriving a signal representative of a characteristic of the culture at each frequency and processing said signals to provide an output indicative of the biovolume.

4. The method of claim 3 in which the characteristic is conductance and the signals are generated by determining for each frequency a signal related to the in-phase component of current within the culture.

5. The method of claim 2 in which the biovolume is determined via a capacitance measurement.

6. The method of claim 2 in which the biovolume determination is subjected to a temperature dependent adjustment.

7. The method of claim 3 in which the gas hold-up determination alternating frequency signal is one of the signals used for deriving biovolume.

8. The method of claim 3 in which the gas hold-up determination alternating frequency signal is a separate high frequency signal not used for deriving biovolume.

9. The method of claim 3 in which at least some of the differing frequency signals are input to the culture simultaneously.

10. The method of claim 3 in which at least some of the differing frequency signals are input to the culture sequentially.

11. The method of claim 1 in which the signals are input by induction electrically to the culture.

12. A method of determining gas hold-up in a fermentation culture having a concentration of biological cells in a biomass, the method comprising, prior to aeration and then during fermentation of the culture, inputting inputting to the culture electrically coupling an alternating signal at a frequency which is within an upper part of the range of frequencies at which β dispersion occurs, determining the magnitude of reactive current signal leading voltage in the culture and using measured difference in said magnitudes determined prior to aeration and determined during fermentation as a measure of the gas hold-up.

13. The method of claim 12 in which a curve fitting technique is used to determined a reactive current signal value above the β dispersion range.

14. The method of claim 12 further comprising determining biovolume in a culture and utilizing said gas hold-up determination to provide a corrected biovolume estimate.

15. The method of claim 14 in which the biovolume is determined by inputting respective high and low frequency alternating signals to the culture, deriving a signal representative of a characteristic of the culture at each frequency and processing said signals to provide an output indicative of the biovolume.

16. The method of claim 15 in which the characteristic is conductance and the signals are generated by determining for each frequency a signal related to the in-phase component of current within the culture.

17. The method of claim 14 in which the biovolume is determined via a capacitance measurement capacitance.

18. The method of claim 14 in which the biovolume determination is subjected to a temperature dependent adjustment.

19. The method of claim 15 in which the gas hold-up determination alternating frequency signal is one of the signals used for deriving biovolume.

20. The method of claim 15 in which the gas hold-up determination alternating frequency signal is a separate high frequency signal not used for deriving biovolume.

21. The method of claim 15 in which at least some of the differing frequency signals are input to the culture simultaneously.

22. The method of claim 15 in which at least some of the differing frequency signals are input to the culture sequentially.

23. The method of claim 12 in which signals are input by induction electrically to the culture.

24. Apparatus for determining gas hold-up in a fermentation culture including biological cells, the apparatus comprising a probe circuit electrically coupled means for inputting to the culture for inputting a high frequency alternating signal at least in the upper portion of the β dispersion range, means for inputting a signal representative of the voltage over the culture to a phase sensitive director, means for imposing a 90° phase lag on a signal representative of current through the culture and for inputting said lagged signal to the phase sensitive detector to produce a signal related to a quadrature component of current in the culture and a difference circuit for receiving a signal related to the quadrature component of current before onset of aeration of the culture and subsequently receiving a signal related to the quadrature component during fermentation and establishing a difference value which is output as a measure of gas hold-up.

25. The apparatus of claim 24 in which said signal is at a frequency above the β dispersion range.

26. The apparatus of claim 24 further comprising means for determining biovolume comprising means for inputting respective high and low frequency alternating signals to the culture and means for generating from the relative magnitude of characteristics of at least one of current and voltage at the respective high and low frequencies an output signal indicative of biovolume.

27. The apparatus of claim 24 in which the alternating signals are input to the culture by induction electrically to the culture via probe circuit.

28. The apparatus of claim 26 in which the means for generating comprises band-pass filters tuned to a respective one of the frequencies and connected to means for obtaining an in-phase component of current signal relative to the respective voltage signal, the outputs of which are input to a difference circuit.

29. The apparatus of claim 28 including means for sampling voltage signals over the culture and means for determining current signals in the culture, the voltage signals being input to the band-pass filters and the current signals input, along with the output from the band-pass filters to the means for obtaining the in-phase component.

30. The apparatus of claim 26 further comprising means for adjusting the output signal indicative of biovolume in dependence upon temperature sensed in the culture.

31. The apparatus of claim 26 further comprising means for adjusting the output signal indicative of biovolume in dependence upon the magnitude of said difference value.

32. Apparatus for determining gas hold-up and providing a corrected biovolume estimate for a concentration of biological cells in a biomass, the apparatus comprising:

means for measuring biovolume comprising means for inputting to the culture via electrode probes electrically coupled to the culture alternating signals at spaced apart frequencies within the β dispersion range and means for generating from the relative magnitude of resulting characteristics of at least one of current and voltage at said spaced apart frequencies an output signal indicative of biovolume; and means for correcting for gas hold-up said output signal indicative of biovolume, said means for correcting comprising means for inputting to the culture a high frequency alternating signal at a frequency at least in the upper part of the β dispersion range and means for generating from the relative magnitude of quadrature components of current within the culture resulting from input of said high frequency signal prior to aeration of the culture and subsequently input during aeration a difference frequency value of alternating signal, and means for adjusting said output signal indicative of biovolume in dependence upon the magnitude of said difference frequency value of quadrature current component.

33. The apparatus of claim 32 in which the high frequency alternating signal is at a frequency above the β dispersion range.

34. The apparatus of claim 32 in which said high frequency signal is also one of said alternating signals at spaced apart frequencies.

35. The apparatus of claim 32 in which at least some of said high frequency signal and signals at spaced apart frequencies are input to the culture simultaneously.

36. The apparatus of claim 32 in which at least some of said high frequency signal and signals at spaced apart frequencies are input to the culture serially.

37. The apparatus of claim 32 further comprising curve fitting means for adjusting said quadrature component of current to a value such that the alternating frequency of the current is above the β dispersion range.

38. The apparatus of claim 24 further comprising curve fitting means for adjusting said quadrature component of current to a value such that the alternating frequency of the current is above the β dispersion range.

* * * * *